United States Patent

Parg et al.

[11] 4,360,672
[45] Nov. 23, 1982

[54] SUBSTITUTED PHENOXYPHENYL PYRIDAZONES, THEIR PREPARATION, AND THEIR USE AS HERBICIDES

[75] Inventors: Adolf Parg, Bad Durkheim; Gerhard Hamprecht, Weinheim; Bruno Wuerzer, Otterstadt, all of Fed. Rep. of Germany

[73] Assignee: BASF Aktiengesellschaft, Fed. Rep. of Germany

[21] Appl. No.: 247,784

[22] Filed: Mar. 26, 1981

[30] Foreign Application Priority Data

Apr. 5, 1980 [DE] Fed. Rep. of Germany ....... 3013267

[51] Int. Cl.³ ................. C07D 237/22; C07D 237/20; C07D 237/14; C07D 237/16
[52] U.S. Cl. ..................................... 544/240; 544/238; 544/241; 71/92
[58] Field of Search ................ 544/238, 239, 240, 241

[56] References Cited

U.S. PATENT DOCUMENTS

| 3,376,128 | 4/1968 | Reichender | 544/240 |
| 3,652,562 | 3/1972 | Reicheneder | 544/240 |
| 4,077,797 | 3/1978 | Fischer | 544/240 |

FOREIGN PATENT DOCUMENTS

| 728164 | 8/1969 | Belgium. |
| 1197676 | 7/1965 | Fed. Rep. of Germany. |
| 2311638 | 9/1973 | Fed. Rep. of Germany. |
| 2526643 | 12/1976 | Fed. Rep. of Germany. |

Primary Examiner—Mark L. Berch
Attorney, Agent, or Firm—Keil & Witherspoon

[57] ABSTRACT

Substituted pyridazones of the general formula

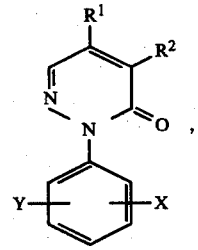

where $R^2$ is halogen or alkoxy, $R^1$ is amino, alkylamino, dialkylamino, alkoxyamino, alkylalkoxyamino, halogen, alkoxy, trimethyleneimino or acylated amino, X is unsubstituted or substituted phenoxy of the formula

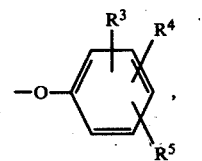

where $R^3$, $R^4$ and $R^5$ are each, independently of one another, hydrogen, halogen, nitro, cyano, carboxyl, alkyl, haloalkyl, alkoxy, haloalkoxy, alkylmercapto, haloalkylmercapto, alkylsulfinyl or alkylsulfonyl and Y is hydrogen, cyano, haloalkyl, halogen or nitro, and herbicides which contain these compounds.

2 Claims, No Drawings

SUBSTITUTED PHENOXYPHENYL PYRIDAZONES, THEIR PREPARATION, AND THEIR USE AS HERBICIDES

The present invention relates to novel valuable substituted pyridazones, their preparation, their use as herbicides, and herbicides which contain these compounds as active ingredients.

It is known that 1-phenyl-4,5-dimethoxy-pyridaz-6-one has a broad herbicidal action and can therefore be used as a total herbicide, without sparing crop plants (German Pat. No. 1,197,676). The active ingredient damages plants both in pre-emergence use and when used to treat leaves.

1-m-Trifluoromethylphenyl-4,5-dimethoxy-pyridaz-6-one has been disclosed to have similar herbicidal properties (Belgian Pat. No. 728,164).

The use of the sodium salt of 2-chloro-4-trifluoromethylphenyl-3'-carboxy-4'-nitrophenyl ether as a herbicide has also been disclosed (German Laid-Open Application DOS 2,311,638).

We have found that substituted pyridazones of the general formula

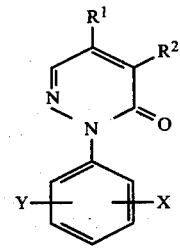

where $R^2$ is halogen or alkoxy of 1 to 3 carbon atoms, $R^1$ is amino, alkylamino, dialkylamino, alkoxyamino or alkylalkoxyamino, where alkyl and alkoxy is in each case of 1 to 3 carbon atoms and the alkyl radicals may be identical or different, halogen (chlorine or bromine), alkoxy of 1 to 3 carbon atoms, trimethyleneimino or amino acylated by $ClH_2CC(O)-$ or $CH_3COOCH_2C(O)-$, X is unsubstituted or substituted phenoxy of the formula

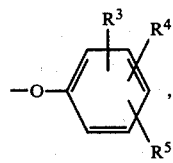

where $R^3$, $R^4$ and $R^5$ are each, independently of one another, hydrogen, halogen, nitro, cyano, carboxyl, alkyl, haloalkyl (trifluoromethyl), alkoxy, haloalkoxy, alkylmercapto, haloalkylmercapto, alkylsulfinyl or alkylsulfonyl, alkyl or alkoxy in each case being of 1 to 4 carbon atoms, and Y is hydrogen, halogen, haloalkyl, cyano or nitro, possess a good herbicidal activity and in addition are surprisingly well tolerated by crop plants. $R^2$ in formula I can be, for example, fluorine, chlorine, bromine, iodine, methoxy, ethoxy or propoxy, and $R^1$ can be, for example, amino, methylamino, ethylamino, dimethylamino, diethylamino, methylethylamino, methoxyamino, methylmethoxyamino, chlorine, bromine, methoxy, ethoxy, propoxy, $ClCH_2C(O)NH-$, $CH_3COOCH_2C(O)NH-$ or trimethyleneimino. X can be, for example, a substituted phenoxy of the formula

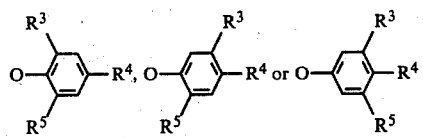

where $R^3$, $R^4$ and $R^5$ can each, for example, be hydrogen, fluorine, chlorine, bromine, iodine, nitro, cyano, carboxyl, methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl or ethylsulfonyl. Y can be, for example, hydrogen, fluorine, chlorine, bromine, iodine, cyano or nitro.

Preferred compounds are those where $R^2$ is, for example, chlorine, bromine or methoxy, $R^1$ is, for example, amino, methylamino, dimethylamino, methylmethoxyamino or methoxy, X is phenoxy which is in the 3- or 4-position of the phenyl radical and is substituted, for example by halogen or haloalkyl, especially by chlorine or trifluoromethyl, and Y is hydrogen or nitro in the 6-position of the phenyl radical.

The pyridazones of the formula I where $R^1$ is other than halogen can be prepared by reacting a dihalopyridazone of the formula II

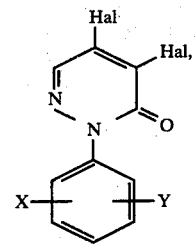

where X and Y have the above meanings and Hal is halogen, especially chlorine or bromine, with not less than twice the stoichiometric amount of an amine of the formula III

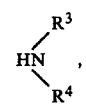

where $R^3$ or $R^4$ is hydrogen, alkyl of 1 to 3 carbon atoms or alkoxy of 1 to 3 carbon atoms, or with about the stoichiometric amount, per halogen to be reacted (it may be intended to react one or both of the halogens), of an alcoholate of the formula IV $MOR^5$      IV, where M is a cation of a metal, especially sodium or potassium, and $R^5$ is alkyl of 1 to 3 carbon atoms (methyl), in the presence of an organic solvent, at from 20° to 150° C., under atmospheric pressure or superatmospheric pressure (from 1 to 10 bar), continuously or batchwise.

If 1-[4'-(3"-trifluoromethyl-phenoxy)]-phenyl-4,5-dichloropyridaz-6-one and sodium methylate are used as the starting materials, the course of the reaction can be represented by the following equation:

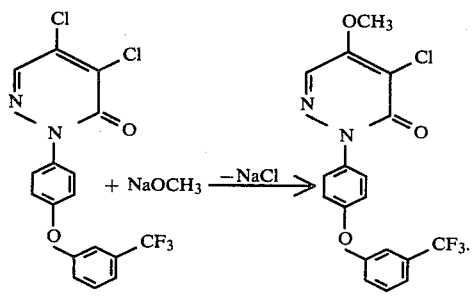

Advantageously, the dihalopyridazone II is first dissolved or suspended in an organic solvent, for example in ethanol, and then reacted with the corresponding amount of alcoholate or amine, which may be in the form of an aqueous alcoholic solution (German Laid-Open Application DOS 2,526,643, German Pat. No. 1,210,241, U.S. Pat. No. 2,628,181 and German Laid-Open Application DOS 1,695,840). The reaction can be carried out under atmospheric or superatmospheric pressure, for example for from 0.5 to 12 hours at from 20° to 150° C., preferably from 50° to 120° C., continuously or batchwise. The reaction mixture is worked up by conventional methods. If the end product is obtained as a solid, it is isolated by, for example, filtering off the precipitate. If, on the other hand, the end product remains in solution in the solvent, the latter is distilled off under reduced pressure and the residue is stirred with water and filtered off. The product can be purified by, for example, recrystallization or chromatography. The dihalopyridazones II employed can be compounds obtained, for example, as follows:

The phenylhydrazines of the formula V

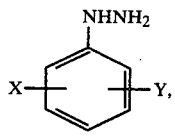

where X and Y have the above meanings, are reacted with a 3-formyl-2,3-dihalo-acrylic acid of the formula VI

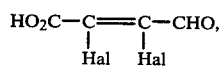

where Hal is halogen, especially chlorine or bromine, preferably at room temperature, in the presence of a solvent, for example in an aqueous mineral acid or in an aqueous or anhydrous inert organic solvent, such as ethanol, which is evaporated off at the end of the reaction; the corresponding dihaloacrylic acid semicarbazone is obtained, and this is cyclized, for example without prior isolation, by boiling in glacial acetic acid or acetic anhydride or by heating in an aqueous mineral acid, for example hydrochloric acid, at from 70° to 100° C., or by stirring in a concentrated mineral acid, for example sulfuric acid, at room temperature (20° C.), to give the corresponding compound of the formula II (German Laid-Open Applications DOS 1,695,840, DOS 2,526,643 and DOS 1,545,595). The process can be carried out continuously or batchwise. The reaction mixture is worked up by conventional methods.

The phenylhydrazines of the formula V, required as starting materials, can be obtained by conventional methods from the corresponding anilines of the formula

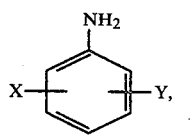

where X and Y have the above meanings, namely by diazotizing in the usual manner and then reducing the diazonium salt (Houben-Weyl, Methoden der organischen Chemie, volume 10/2, page 180, Georg-Thieme-Verlag, Stuttgart, 1967). The conversion to the corresponding pyrazone can, for example, be carried out without isolating the phenylhydrazine, but purer end products are obtained if the phenylhydrazine is isolated as the hydrochloride.

The anilines of the general formula VII can, in the case of 4-phenoxy-substituted derivatives, be prepared by conventional methods (German Laid-Open Applications DOS 2,538,178 and DOS 2,411,320), whilst the 3-phenoxy-substituted derivatives are known (Liebigs Ann. Chem. 740 (1970), 169–179) or can be prepared by the conventional methods.

The Examples which follow illustrate the preparation of the novel compounds of the formula I. Parts by weight bear the same relation to parts by volume as that of the kilogram to the liter.

EXAMPLE 1

25.3 parts by weight of 4-(3'-trifluoromethylphenoxy)-aniline suspended in 230 parts by volume of concentrated hydrochloric acid are diazotized with 6.9 parts by weight of $NaNO_2$ in 30 parts by volume of $H_2O$ at 0° C., and the product is then reduced with 45 parts by weight of $SnCl_2$ to give 4-(3'-trifluoromethylphenoxy)-phenylhydrazine hydrochloride. The hydrochloride is suspended in 400 parts by volume of 2 N hydrochloric acid, 16.7 parts by weight of mucochloric acid are added and the mixture is kept for 1 hour at 90° C. When it has cooled, the hydrochloric acid is separated from the organic phase, 160 parts by volume of glacial acetic acid are added to the latter, and this mixture is stirred for 10 minutes after reflux. It is then cooled and water is then added to the reaction mixture. The 1-[4'-(3"-trifluoromethyl-phenoxy)]-phenyl-4,5-dichloro-pyridaz-6-one formed is filtered off and recrystallized from methanol (No. 1).

Yield: 28.9 parts by weight (72% of theory).

Melting point: 115°–117° C.

EXAMPLE 2

28.7 parts by weight of 3-(2'-chloro-4'-trifluoromethylphenoxy)-aniline are nitrosylated in 200 parts by volume of glacial acetic acid by means of a solution of 7.6 parts by weight of $NaNO_2$ in 50 parts by volume of concentrated $H_2SO_4$ at 10°–20° C. The diazonium salt solution is reduced direct to the corresponding hydrazine with 45.5 parts by weight of $SnCl_2$ dissolved in 31 parts by volume of concentrated hydrochloric acid. After having added 16.7 parts by weight of mucochloric acid, the reaction solution is stirred for 10 minutes at the boil and is then cooled, and 1,000 parts by volume of water are added. The oily residue is dissolved in $CH_2Cl_2$, the solution is dried with $MgSO_4$, the solvent is evaporated off and the residue is crystallized by trituration with methanol. 32 parts by weight (74% of theory) of 1-[3'-(2''-chloro-4''-trifluoromethyl-phenoxy)]-phenyl-4,5-dichloro-pyridaz-6-one, of melting point 89°–92° C. (No. 2) are obtained.

EXAMPLE 3

20 parts by weight of 1-[4'-(3''-trifluoromethyl-phenoxy)]-phenyl-4,5-dichloro-pyridaz-6-one and 4 parts by weight of sodium methylate in 80 parts by volume of methanol are refluxed for one hour. The reaction mixture is evaporated to dryness and the residue is stirred with water and filtered off. After recrystallization from methanol, 32 parts by weight (80% of theory) of 1-[4'-(3''-trifluoromethyl-phenoxy)]-phenyl-4-methoxy-5-chloro-pyridaz-6-one of melting point 113°–114° C. (No. 3) are obtained.

EXAMPLE 4

10 parts by weight of 1-[3'-(2''-chloro-4''-trifluoromethylphenoxy)]-phenyl-4,5-dichloro-pyridaz-6-one and 6.3 parts by weight of sodium methylate in 100 parts by volume of absolute toluene are boiled for one hour. The mixture is then filtered hot and the filtrate is evaporated to dryness. The oily residue is triturated with diisopropyl ether, and on filtration 3.9 parts by weight (35% of theory) of 1-[3'-(2'''-chloro-4''-trifluoromethylphenoxy)]-phenyl-4,5-dimethoxy-pyridaz-6-one, of melting point 72°–79° C., are obtained (No. 4).

EXAMPLE 5

26 parts by weight of 1-[3'-(2''-chloro-4''-trifluoromethylphenoxy)]-phenyl-4,5-dichloropyridaz-6-one and 16 parts by weight of methylamine dissolved in 100 parts by volume of ethanol are boiled for 1 hour. The mixture is filtered hot, the filtrate is concentrated to dryness and the residue is stirred with water. It is then filtered off and recrystallized from methanol, giving 15 parts by weight (58% of theory) of 1-[3'-(2''-chloro-4''-trifluoromethylphenoxy)]-phenyl-4-methylamino-5-chloro-pyridaz-6-one of melting point 186°–188° C. (No. 5).

EXAMPLE 6

A solution of 20 parts by weight of 1-[3'-(2''-chloro-4''-trifluoromethylphenoxy)]-phenyl-4,5-dichloropyridaz-6-one in 300 parts by volume of glacial acetic acid is nitrated with a mixture of 5.6 parts by weight of $HNO_3$ (density 1.40) and 5.9 parts by weight of concentrated $H_2SO_4$ at 0°–5° C. The mixture is stirred for 2 hours at 5° C. and 1,000 parts by weight of water are then added. The precipitate is filtered off and recrystallized from diisopropyl ether. 13.3 parts by weight (60% of theory) of 1-[3'-(2''-chloro-4''-trifluoromethylphenoxy)-6'-nitro]-phenyl-4,5-dichloropyridaz-6-one of melting point 128°–130° C. (No. 6) are obtained.

EXAMPLE 7

15 parts by weight of 1-[3'-(2''-chloro-4''-trifluoromethylphenoxy)-6'-nitro]-phenyl-4,5-dichloropyridaz-6-one and 200 parts by volume of concentrated $NH_3$ solution are heated for 12 hours at 100° C. in an autoclave under the autogenous pressure. The residue is filtered off and recrystallized from methanol, giving 10 parts by weight (72% of theory) of 1-[3'-(2''-chloro-4''-trifluoromethyl-phenoxy)-6'-nitro]-phenyl-4-amino-5-chloro-pyridaz-6-one of melting point 227°–230° C. (No. 7).

The compounds shown in the Table which follows are prepared by methods similar to Examples 1 to 7.

| Ex. no. | X | Position X | Y | $R^1$ | $R^2$ | M.p. [°C.] $n_D^{25}$ Band wavelength in infrared spectrum |
|---|---|---|---|---|---|---|
| 8 | 2-chloro-4-trifluoro-methyl-phenoxy | 3 | H | $NH_2$ | Cl | 204–206 |
| 9 | 2-chloro-4-trifluoro-methyl-phenoxy | 4 | " | " | " | |
| 10 | 2-chloro-4-trifluoro-methyl-phenoxy | 3 | " | $OCH_3$ | " | 112–115 |
| 11 | 2-chloro-4-trifluoro-methyl-phenoxy | 4 | " | " | " | |
| 12 | 2-chloro-4-trifluoro-methyl-phenoxy | 3 | " | 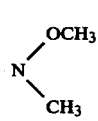 | " | 78–82 |
| 13 | 2-chloro-4-trifluoro-methyl-phenoxy | 4 | " | " | " | |
| 14 | 2-chloro-4-trifluoro-methyl-phenoxy | 4 | " | $OCH_3$ | $OCH_3$ | |
| 15 | 2-chloro-4-trifluoro-methyl-phenoxy | 4 | " | Cl | Cl | |

-continued

| Ex. no. | X | Position X | Y | R¹ | R² | M.p. [°C.] $n_D^{25}$ Band wavelength in infrared spectrum |
|---|---|---|---|---|---|---|
| 16 | 2-chloro-4-trifluoro-methyl-phenoxy | 3 | " | N(CH₃)(CH₃) | " | |
| 17 | 2-chloro-4-trifluoro-methyl-phenoxy | 4 | " | " | " | |
| 18 | 3-chloro-4-trifluoro-methyl-phenoxy | 3 | " | Cl | " | C=O 1670 cm⁻¹ |
| 19 | 3-chloro-4-trifluoro-methyl-phenoxy | 4 | " | " | " | $n_D^{25}$ 1.5883 |
| 20 | 3-chloro-4-trifluoro-methyl-phenoxy | 3 | " | OCH₃ | " | 1.5987 |
| 21 | 3-chloro-4-trifluoro-methyl-phenoxy | 4 | " | " | " | |
| 22 | 3-chloro-4-trifluoro-methyl-phenoxy | 3 | " | " | OCH₃ | C=O 1650 cm⁻¹ |
| 23 | 3-chloro-4-trifluoro-methyl-phenoxy | 4 | " | " | " | 1.5749 |
| 24 | 3-chloro-4-trifluoro-methyl-phenoxy | 3 | " | NH₂ | Cl | 154–158 |
| 25 | 3-chloro-4-trifluoro-methyl-phenoxy | 4 | " | " | " | |
| 26 | 3-chloro-4-trifluoro-methyl-phenoxy | 3 | " | N(OCH₃)(CH₃) | " | |
| 27 | 3-chloro-4-trifluoro-methyl-phenoxy | 4 | " | " | " | |
| 28 | 3-chloro-4-trifluoro-methyl-phenoxy | 3 | " | N(CH₃)(CH₃) | " | |
| 29 | 3-chloro-4-trifluoro-methyl-phenoxy | 4 | " | " | " | |
| 30 | 2,4-dichlorophenoxy | 3 | " | Cl | " | |
| 31 | " | 4 | " | " | " | 122–124 |
| 32 | " | 3 | " | OCH₃ | " | |
| 33 | " | 4 | " | " | " | |
| 34 | " | 3 | " | " | OCH₃ | |
| 35 | " | 4 | " | " | " | 126–131 |
| 36 | " | 3 | " | N(OCH₃)(CH₃) | Cl | |
| 37 | " | 4 | " | N(OCH₃)(CH₃) | " | |
| 38 | 2,6-dichloro-4-trifluoro-methyl-phenoxy | 3 | " | Cl | " | |
| 39 | 2,6-dichloro-4-trifluoro-methyl-phenoxy | 4 | " | " | " | |
| 40 | 2,6-dichloro-4-trifluoro-methyl-phenoxy | 3 | " | OCH₃ | " | |
| 41 | 2,6-dichloro-4-trifluoro-methyl-phenoxy | 4 | " | " | " | |
| 42 | 2,6-dichloro-4-trifluoro-methyl-phenoxy | 3 | " | " | OCH₃ | |
| 43 | 2,6-dichloro-4-trifluoro-methyl-phenoxy | 4 | " | " | " | |
| 44 | 2,6-dichloro-4-trifluoro-methyl-phenoxy | 3 | " | N(OCH₃)(CH₃) | Cl | |
| 45 | 2,6-dichloro-4-trifluoro- | 4 | " | " | " | |

-continued

| Ex. no. | X | Position X | Y | R¹ | R² | M.p. [°C.] $n_D^{25}$ Band wavelength in infrared spectrum |
|---|---|---|---|---|---|---|
| | methyl-phenoxy | | | | | |
| 46 | 2,4,6-trichlorophenoxy | 3 | " | Cl | " | |
| 47 | " | 4 | " | " | " | |
| 48 | " | 3 | " | OCH₃ | " | |
| 49 | " | 4 | " | " | " | |
| 50 | " | 3 | " | " | OCH₃ | |
| 51 | " | 4 | " | " | " | |
| 52 | " | 3 | " | N(CH₃)(OCH₃) | Cl | |
| 53 | " | 4 | " | " | " | |
| 54 | 2,4-difluorophenoxy | 3 | " | OCH₃ | OCH₃ | |
| 55 | " | 4 | " | " | " | |
| 56 | 2-chloro-4-fluorophenoxy | 3 | " | " | " | |
| 57 | " | 4 | " | " | " | |
| 58 | 2,4-dibromophenoxy | 3 | " | " | " | |
| 59 | " | 4 | " | " | " | |
| 60 | 2-chloro-4-nitro-phenoxy | 3 | " | " | " | |
| 61 | " | 4 | " | " | " | |
| 62 | 2-chloro-4-cyanophenoxy | 3 | " | " | " | |
| 63 | " | 4 | " | " | " | |
| 64 | 2-chloro-4-methylmercapto-phenoxy | 3 | " | " | " | |
| 65 | 2-chloro-4-methylmercapto-phenoxy | 4 | " | " | " | |
| 66 | 2-nitro-4-trifluoromethyl-phenoxy | 3 | " | " | " | |
| 67 | 2-nitro-4-trifluoromethyl-phenoxy | 4 | " | " | " | |
| 68 | 3-trifluoromethyl-4-chlorophenoxy | 3 | " | " | " | |
| 69 | 3-trifluoromethyl-4-chlorophenoxy | 4 | " | " | " | |
| 70 | 3-trifluoromethyl-4-nitro-phenoxy | 3 | " | " | " | |
| 71 | 3-trifluoromethyl-4-nitro-phenoxy | 4 | " | " | " | |
| 72 | 3,5-dichloro-4-trifluoromethyl-phenoxy | 3 | " | " | " | |
| 73 | 3,5-dichloro-4-trifluoromethyl-phenoxy | 4 | " | " | " | |
| 74 | 3-fluoro-4-trifluoromethyl-phenoxy | 3 | " | " | " | |
| 75 | 3-fluoro-4-trifluoromethyl-phenoxy | 4 | " | " | " | |
| 76 | 3-cyano-4-trifluoromethyl-phenoxy | 3 | " | " | " | |
| 77 | 3-cyano-4-trifluoromethyl-phenoxy | 4 | " | " | " | |
| 78 | 2,5-dichloro-4-trifluoromethyl-phenoxy | 3 | " | " | " | |
| 79 | 2,5-dichloro-4-trifluoromethyl-phenoxy | 4 | " | " | " | |
| 80 | 2-chloro-4-trifluoromethoxy-phenoxy | 3 | " | " | " | |
| 81 | 2-chloro-4-trifluoromethoxy-phenoxy | 4 | " | " | " | |
| 82 | 2,6-dichloro-4-trifluoromethoxy-phenoxy | 3 | " | " | " | |
| 83 | 2,6-dichloro-4-trifluoromethoxy-phenoxy | 4 | " | " | " | |
| 84 | 2-chloro-4-difluoromethyl-phenoxy | 3 | " | " | " | |
| 85 | 2-chloro-4-difluoromethyl-phenoxy | 4 | " | " | " | |
| 86 | 2-methyl-4-chloro-phenoxy | 3 | " | " | " | |
| 87 | " | 4 | " | " | " | |
| 88 | 3-trifluoromethyl-phenoxy | 3 | " | " | " | |
| 89 | " | 4 | " | " | " | 84–85 |
| 90 | " | 3 | " | NHCH₃ | Cl | |
| 91 | " | 4 | " | " | " | 131–134 |
| 92 | " | 3 | " | NH₂ | " | |
| 93 | " | 4 | " | " | " | 175–177 |
| 94 | 4-chlorophenoxy | 4 | 3-CF₃ | Cl | Cl | 129–131 |
| 95 | " | 4 | " | OCH₃ | " | 168–170 |

-continued

| Ex. no. | X | Position X | Y | R¹ | R² | M.p. [°C.] $n_D^{25}$ Band wavelength in infrared spectrum |
|---|---|---|---|---|---|---|
| 96 | " | 4 | " | " | OCH₃ | 98–100 |
| 97 | " | 4 | " | NHCH₃ | Cl | 156–158 |
| 98 | " | 4 | " | NH₂ | " | 199–201 |
| 99 | 2-chloro-4-trifluoro-methyl-phenoxy | 3 | 6-NO₂ | NHCCH₂Cl‖O | Cl | |
| 100 | 2-chloro-4-trifluoro-methyl-phenoxy | 3 | " | OCH₃ | " | 179–181 |
| 101 | 2-chloro-4-trifluoro-methyl-phenoxy | 3 | 6-NO₂ | OCH₃ | OCH₃ | 128–131 |
| 102 | 2-chloro-4-trifluoro-methyl-phenoxy | 3 | " | NHCH₃ | Cl | 164–167 |
| 103 | 2-chloro-4-trifluoro-methyl-phenoxy | 3 | " | N(CH₃)₂ | Cl | 155–159 |
| 104 | 2-chloro-4-trifluoro-methyl-phenoxy | 3 | " | N(OCH₃)(CH₃) | Cl | 167–171 |
| 105 | 2-chloro-4-trifluoro-methyl-phenoxy | 3 | 6-Cl | Cl | " | |
| 106 | 2-chloro-4-trifluoro-methyl-phenoxy | 3 | " | OCH₃ | " | |
| 107 | 2-chloro-4-trifluoro-methyl-phenoxy | 3 | " | OCH₃ | OCH₃ | |
| 108 | 2,6-dichloro-4-trifluoromethyl-phenoxy | 3 | 6-NO₂ | " | " | |
| 109 | 2,4-dichlorophenoxy | 3 | " | " | " | |
| 110 | 2,4,6-trichlorophenoxy | 3 | " | " | " | |
| 111 | 3-chloro-4-trifluoromethyl-phenoxy | 3 | H | NHCH₃ | H | C=O = 1620 cm⁻¹ |
| 112 | 2,5-dichlorophenoxy | 4 | " | Cl | Cl | 81–84 |
| 113 | " | 4 | " | OCH₃ | OCH₃ | 98–103 |
| 114 | 3-bromophenoxy | 4 | " | Cl | Cl | 110–113 |
| 115 | " | 4 | " | OCH₃ | OCH₃ | 96–99 |
| 116 | 2-bromo-4-chlorophenoxy | 4 | " | Cl | Cl | 128–131 |
| 117 | 2-bromo-4-chloro-phenoxy | 4 | " | OCH₃ | OCH₃ | 111–115 |
| 118 | 2-bromo-4-fluoro-phenoxy | 4 | " | Cl | Cl | 91–93 |
| 119 | " | 4 | " | OCH₃ | OCH₃ | 100–105 |
| 120 | 3,4-dichlorophenoxy | 4 | " | Cl | Cl | 137–142 |
| 121 | " | 4 | " | OCH₃ | OCH₃ | 101–103 |
| 122 | 3-trifluoromethoxyphenoxy | 4 | " | Cl | Cl | 84–89 |
| 123 | " | 4 | " | OCH₃ | OCH₃ | 58–63 |
| 124 | 3-tert.butylphenoxy | 4 | " | Cl | Cl | 76–77 |
| 125 | " | 4 | " | OCH₃ | OCH₃ | 1.5768 |
| 126 | 3-methoxyphenoxy | 4 | " | Cl | Cl | 97–101 |
| 127 | " | 4 | " | OCH₃ | OCH₃ | 71–76 |
| 128 | 4-chloro-3-methylphenoxy | 4 | " | Cl | Cl | 160–163 |
| 129 | " | 4 | " | OCH₃ | OCH₃ | 83–86 |
| 130 | 3-methylphenoxy | 4 | " | Cl | Cl | 130–132 |
| 131 | " | 4 | " | OCH₃ | OCH₃ | 79–81 |
| 132 | 2-chloro-5-methylphenoxy | 4 | " | Cl | Cl | 88–92 |
| 133 | " | 4 | " | OCH₃ | OCH₃ | 109–112 |
| 134 | 2-chloro-4-bromophenoxy | 4 | " | Cl | Cl | 130–132 |
| 135 | " | 4 | " | OCH₃ | OCH₃ | 138–140 |
| 136 | 3-fluorophenoxy | 4 | " | Cl | Cl | 130–133 |
| 137 | " | 4 | " | OCH₃ | OCH₃ | 84–88 |
| 138 | 3-trifluoromethylphenoxy | 4 | 3-Cl | Cl | Cl | 105–109 |
| 139 | " | 4 | " | OCH₃ | OCH₃ | 82–89 |
| 140 | " | 4 | 3-CF₃ | Cl | Cl | 84–89 |
| 141 | " | 4 | " | OCH₃ | OCH₃ | 75–82 |
| 142 | " | 4 | " | NHCH₃ | Cl | C=O 1620 cm⁻¹ |
| 143 | 2-chloro-4-trifluoromethylphenoxy | 3 | 6-NO₂ | NH—C₃H₇(i) | Cl | 170–176 |
| 144 | 2-chloro-4-trifluoromethylphenoxy | 3 | " | N(C₂H₅)₂ | Cl | 142–143 |

The influence of representatives of the novel phenoxy-substituted pyzidazones on the growth of unwanted plants is demonstrated in greenhouse experiments.

The vessels employed were plastic flowerpots having a volume of 300 cm³, and which were filled with a sandy loam containing about 1.5% humus. The seeds of the test plants given in Table 1 were sown shallow, and separately, according to species.

In the preemergence treatment, the active ingredients were immediately applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, either plants which were sown directly in the pots and grew there were selected, or plants which were grown separately as seedlings and transplanted to the experiment vessels a few days before treatment. The amounts of active ingredient applied in this treatment were equivalent to 0.25 and 0.5 kg/ha. For comparison purposes, the prior art active ingredients 1-phenyl-4,5-dimethoxypyridaz-6-one (A), 1-m-trifluoromethylphenyl-4,5-dimethoxypyridaz-6-one (B) and 2-chloro-4-trifluoromethylphenyl-3'-carboxy-4'-nitrophenyl ether, sodium salt (C) were employed in the same amounts.

No cover was placed on the vessels. The pots were set up in the greenhouse-species from warmer areas at from 20° to 30° C., and species from moderate climates at 15° to 25° C. The experiments were run for from 2 to 4 weeks. During this period, the plants were tended and their reactions to the various treatments assessed.

The results obtained in the experiments show that the novel compounds, in the preferred postemergence treatment, have, overall, a similar action to that of the prior art compound used for comparison purposes, and a superior herbicidal action on some unwanted species. However, what should be particularly emphasized is the fact that the new compounds are tolerated much better by crop plants, preferably from the Gramineae family. When the compounds are applied preemergence, a herbicidal action is also observed.

If certain crop plants are fairly sensitive to the active ingredients, special application techniques may be employed in which the agents are sprayed with the aid of spraying equipment in such a way that the leaves of sensitive crop plants are if possible not hit; the active ingredients reach the soil or unwanted plants growing below the crop plants (post-directed, lay-by treatment).

In view of the fact that crop plants tolerate the new compounds well, and the many possible methods of applying them, the agents according to the invention, or mixtures containing them, may be used in addition to the crop plants listed in the tables in a large number of other crops for eliminating unwanted growth. Application rates may vary from 0.1 to 15 kg/ha and more.

The following crop plants are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |

| Botanical name | Common name |
| --- | --- |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of activity and to achieve synergistic effects, the novel phenoxy-substituted pyridazones may be mixed among themselves or with numerous representatives of other herbicidal or growth-regulating active ingredient groups and applied in such mixtures. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-$\alpha,\alpha,\beta,\beta$-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2-(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
ethyl-N-(3-(N'-phenylcarbamoyloxy)-phenyl)-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenyl-carbamate
ethyl N-3-(2'-methylphenoxycarbonylamino)-phenyl-carbamate
methyl N-3-(4'-fluorophenoxycarbonylamino)-phenyl-thiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
$\alpha,\alpha$-dichloropropionic acid, sodium salt
$\alpha,\alpha$-dichlorobutyric acid, sodium salt
$\alpha,\alpha$-$\beta,\beta$-tetrafluoropropionic acid, sodium salt
$\alpha$-methyl-$\alpha,\beta$-dichloropropionic acid, sodium salt
methyl $\alpha$-chloro-$\beta$-(4-chlorophenyl)-propionate
methyl $\alpha,\beta$-dichloro-$\beta$-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]ethane (salts)
1-(4-chlorophenoxy)-3,3-dimethyl-1-(1H-1,2,3-triazol-1-yl)butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(2-n-propoxyethyl)-2-chloroacetanilide
2-(2-methyl-4-chlorophenoxy-N-methoxyacetamide
2-(-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)

2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-($\alpha,\alpha$-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-($\alpha,\alpha,\beta,\beta$-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethyl-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamine
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonylcyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
2,5,6-trichloro-2-pyridinyl-oxyacetic acid (salts, esters, amides)
methyl $\alpha$-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.-butyl-3-(2,4-dichloro-5-isopropoxyphenyl)-1,3,4-oxadiazolone-(2)

4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3-ethoxycarbonyl-4'-nitrophenyl ether
1-(4-benzoyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methyl-pyrazole
3-anilino-4-methoxycarbonyl-5-methylpyrazole
3-tert.butylamino-4-methoxycarbonyl-5-methyl-pyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitro-phenyl ether
2-chloro-4-trifluoromethylphenyl-3(ethoxycarbonyl)-methylthio-4-nitrophenyl ether
2,4,6-trichlorophenyl-3'-(ethoxycarbonyl)-methylthio-4-nitro-phenyl ether
2-[1-(N-ethoxyamino)-butylidene]-5-(2-ethylthio-propyl)-3-hydroxy-cyclohex-2-en-1-one (salts)
2-[1-(N-ethoxyamino)-butylidene]-5-(2-phenylthio-propyl)-3-hydroxy-cyclohex-2-en-1-one (salts)
4-[4-(4'-trifluoromethyl)-phenoxy]-pentene-2-carboxylic acid ethyl ester
2-chloro-4-trifluoromethyl-3'-methoxycarbonyl-4'-nitrophenyl ether
2,4-dichlorophenyl-3'-carboxy-4'-nitrophenyl ether (salts)
4,5-dimethoxy-2-(3-α,α,β-trifluoro-β-bromoethoxy-phenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1(3-chloro-4-ethoxyphenyl)-3,3-dimethylurea
ethyl 2-methyl-4-chlorophenoxythioacetate It may also be useful to apply the mixture according to the invention, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. Non-phytotoxic oils and oil concentrates may also be added.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

EXAMPLE a 90 parts by weight of compound 1 is mixed with 10 parts by weight of N-methyl-α-pyrrolidone. A mixture is obtained which is suitable for application in the form of very fine drops.

EXAMPLE b 20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE c 20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE d 20 parts by weight of compound 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE e 20 parts by weight of compound 1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE f 3 parts by weight of compound 2 is intimately mixed with 97 parts by weight of particulate kaolin. A dust is obtained containing 3% by weight of the active ingredient.

EXAMPLE g 30 parts by weight of compound 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE h 40 parts by weight of compound 4 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

EXAMPLE i 20 parts of compound 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In investigations into the selective herbicidal action at a rate of 0.25 kg of active ingredient per hectare (postemergence treatment in the greenhouse), new compound no. 4 proved to have a superior selective herbicidal action to that of prior art compound A.

In selective weed control at a rate of 0.5 kg of active ingredient per hectare (postemergence treatment in the greenhouse), new compound 88 proved to have a herbicidal action superior to that of prior art compound B.

In investigations into the herbicidal action at a rate of 3 kg of active ingredient per hectare (preemergence treatment in the greenhouse), new compounds 4 and 88 prove to have an excellent herbicidal action.

In investigations into the herbicidal action at a rate of 0.25 kg of active ingredient per hectare (postemergence treatment in the greenhouse), new compound 88 proved to have a selective herbicidal action superior to that of prior art compound B.

In investigations into the herbicidal action at rates of 0.5 and 0.25 kg of active ingredient per hectare (postemergence treatment in the greenhouse), new compounds 7 and 102 exhibited a selective herbicidal action superior to that of prior art compound C.

In investigations into the herbicidal action at a rate of 0.5 kg of active ingredient per hectare (postemergence treatment in the greenhouse), compounds 87 and 126 exhibited a good herbicidal action.

In investigations into the herbicidal action at a rate of 0.25 kg of active ingredient per hectare (postemergence treatment in the greenhouse), compounds 22 and 101 exhibited a good herbicidal action.

We claim:

1. A substituted pyridazone of the formula

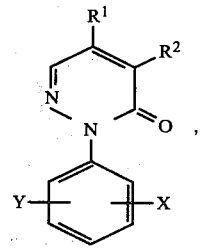

where $R^2$ is halo or alkoxy of 1 to 3 carbon atoms, $R^1$ is amino, alkylamino, dialkylamino, alkoxyamino or alkylalkoxyamino, where alkyl and alkoxy is in each case of 1 to 3 carbon atoms and the alkyl radicals may be identical or different, halogen, alkoxy of 1 to 3 carbon atoms, trimethyleneimino or amino acylated by $ClH_2CC(O)-$ or $CH_3COOCH_2C(O)-$, X is substituted phenoxy of the formula

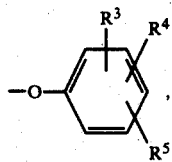

where $R^3$, $R^4$ and $R^5$ are each, independently of one another, hydrogen, halo, nitro, cyano, carboxyl, alkyl, haloalkyl, alkoxy, haloalkoxy, alkylmercapto, haloalkylmercapto, alkylsulfinyl or alkylsulfonyl, alkyl or alkoxy in each case being of 1 to 4 carbon atoms, and Y is hydrogen, halo, haloalkyl, cyano or nitro.

2. A pyridazone as claimed in claim 1, selected from the group consisting of 1-[3'-(2''-chloro-4''-trifluoromethyl-phenoxy)]-phenyl-4,5-dimethoxy-pyridaz-6-one, 1-[3'-(3''-chloro-4''-trifluoromethyl-phenoxy)]-phenyl-4,5-dimethoxy-pyridaz-6-one, 1-[4'-(3''-trifluoromethyl-phenoxy)]-phenyl-4,5-dimethoxy-pyridaz-6-one, 1-[3'-(2''-chloro-4''trifluoromethyl-phenoxy)-6'-nitro]-phenyl-4,5-dimethoxy-pyridaz-6-one, and 1-[3'-(2''-chloro-4''-trifluoromethyl-phenoxy)-6'-nitro]-phenyl-4,5-dichloro-pyridaz-6-one.

* * * * *